US012763196B2

(12) United States Patent
Suzuki et al.

(10) Patent No.: US 12,763,196 B2
(45) Date of Patent: Oct. 13, 2026

(54) MEDICAL INSTRUMENT CONTROL SYSTEM, CONTROL DEVICE, MANAGEMENT SERVER, AND MEDICAL INSTRUMENT CONTROL METHOD

(71) Applicant: OLYMPUS CORPORATION, Tokyo (JP)

(72) Inventors: Takeo Suzuki, Tokyo (JP); Haruna Tadakoshi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 505 days.

(21) Appl. No.: 18/220,925

(22) Filed: Jul. 12, 2023

(65) Prior Publication Data

US 2023/0352160 A1 Nov. 2, 2023

Related U.S. Application Data

(63) Continuation of application No. PCT/JP2021/022748, filed on Jun. 15, 2021.

(51) Int. Cl.
*G16H 40/40* (2018.01)
*G16H 40/67* (2018.01)

(52) U.S. Cl.
CPC ............. *G16H 40/40* (2018.01); *G16H 40/67* (2018.01)

(58) Field of Classification Search
None
See application file for complete search history.

(56) References Cited

U.S. PATENT DOCUMENTS

| | | | | |
|---|---|---|---|---|
| 10,226,163 | B2 | 3/2019 | Lucien, Jr. | |
| 2015/0029001 | A1* | 1/2015 | Pleshek | H04W 4/80 340/10.5 |
| 2020/0405311 | A1* | 12/2020 | Shelton, IV | A61B 17/1155 |
| 2021/0060243 | A1* | 3/2021 | Dave | A61M 5/172 |

FOREIGN PATENT DOCUMENTS

| | | | |
|---|---|---|---|
| JP | H0835889 | A * | 7/1994 |
| JP | H108-35889 | A | 2/1996 |
| JP | 2013-097761 | A | 5/2013 |
| JP | 2018063516 | A | 4/2018 |
| WO | 2021/063877 | A1 | 4/2021 |

OTHER PUBLICATIONS

Zubair AR. Biomedical instruments: safety, quality control, maintenance, prospects and benefits of African technology. Afr J Med Med Sci. Dec. 2010;39 Suppl:35-40. PMID: 22416642.*

(Continued)

*Primary Examiner* — Katherine Kolosowski-Gager
(74) *Attorney, Agent, or Firm* — Scully, Scott, Murphy & Presser, P.C.

(57) ABSTRACT

An accommodating container accommodates a medical instrument. A sensor unit acquires environmental information obtained at the time transportation of the accommodating container. A recording unit records the environmental information acquired by the sensor unit. A control device controls the functions of a medical instrument. The control device restricts the functions of the medical instrument based on the environmental information recorded in the recording unit.

19 Claims, 16 Drawing Sheets

(56) References Cited

OTHER PUBLICATIONS

International Search Report dated Sep. 21, 2021 received in PCT/JP2021/022748.
International Preliminary Report on Patentability dated Dec. 14, 2023 and Written Opinion of the International Searching Authority dated Sep. 21, 2021 received in PCT/JP2021/022748.
Japanese Office Action dated May 21, 2024 received in 2023-528824.
Chinese Office Action dated Apr. 1, 2026 received in 202180097938.8.

* cited by examiner

FIG.6

| SCOPE ID | SCOPE TYPE | LOWEST TEMPERATURE | HIGHEST TEMPERATURE |
|---|---|---|---|
| 1001 | FIRST TYPE | 15°C | 42°C |
| 1002 | FIRST TYPE | 15°C | 42°C |
| 1003 | FIRST TYPE | 15°C | 42°C |
| 1004 | FIRST TYPE | 15°C | 42°C |
| 2001 | SECOND TYPE | 15°C | 42°C |
| 2002 | SECOND TYPE | 15°C | 42°C |
| 2003 | SECOND TYPE | 15°C | 42°C |
| 2004 | SECOND TYPE | 15°C | 42°C |
| 3001 | THIRD TYPE | 15°C | 42°C |
| 3002 | THIRD TYPE | 15°C | 42°C |
| 3003 | THIRD TYPE | 15°C | 42°C |
| 3004 | THIRD TYPE | 15°C | 42°C |

70

FIG.7

| SCOPE TYPE | SET ENVIRONMENTAL CONDITION | |
|---|---|---|
| | LOWER TEMPERATURE LIMIT | UPPER TEMPERATURE LIMIT |
| FIRST TYPE | 0°C | 50°C |
| SECOND TYPE | 0°C | 40°C |
| THIRD TYPE | −30°C | 50°C |

66

FIG.8

| SCOPE ID | SCOPE TYPE | LOWEST TEMPERATURE | HIGHEST TEMPERATURE | AUTHORIZATION INFORMATION |
|---|---|---|---|---|
| 1001 | FIRST TYPE | 15°C | 42°C | PERMITTED |
| 1002 | FIRST TYPE | 15°C | 42°C | PERMITTED |
| 1003 | FIRST TYPE | 15°C | 42°C | PERMITTED |
| 1004 | FIRST TYPE | 15°C | 42°C | PERMITTED |
| 2001 | SECOND TYPE | 15°C | 42°C | NOT PERMITTED |
| 2002 | SECOND TYPE | 15°C | 42°C | NOT PERMITTED |
| 2003 | SECOND TYPE | 15°C | 42°C | NOT PERMITTED |
| 2004 | SECOND TYPE | 15°C | 42°C | NOT PERMITTED |
| 3001 | THIRD TYPE | 15°C | 42°C | PERMITTED |
| 3002 | THIRD TYPE | 15°C | 42°C | PERMITTED |
| 3003 | THIRD TYPE | 15°C | 42°C | PERMITTED |
| 3004 | THIRD TYPE | 15°C | 42°C | PERMITTED |

70

20

| SENSOR UNIT ID | LOWEST TEMPERATURE | HIGHEST TEMPERATURE |
|---|---|---|
| ab123 | 15°C | 42°C |

FIG.11

| SENSOR UNIT ID | SCOPE ID |
|---|---|
| ab123 | 1001 |
| | 1002 |
| | 1003 |
| | 1004 |
| | 2001 |
| | 2002 |
| | 2003 |
| | 2004 |
| | 3001 |
| | 3002 |
| | 3003 |
| | 3004 |

70

FIG.15

| SCOPE ID | SCOPE TYPE | LOWEST TEMPERATURE | HIGHEST TEMPERATURE |
|---|---|---|---|
| 1001 | FIRST TYPE | 15.1°C | 42.1°C |
| 1002 | FIRST TYPE | 14.8°C | 42°C |
| 1003 | FIRST TYPE | 14.9°C | 41.9°C |
| 1004 | FIRST TYPE | 15°C | 41.8°C |
| 2001 | SECOND TYPE | 15°C | 42°C |
| 2002 | SECOND TYPE | 15°C | 42°C |
| 2003 | SECOND TYPE | 14.9°C | 41.8°C |
| 2004 | SECOND TYPE | 15°C | 42°C |
| 3001 | THIRD TYPE | 15°C | 42°C |
| 3002 | THIRD TYPE | 15.1°C | 42.1°C |
| 3003 | THIRD TYPE | 15.1°C | 42.1°C |
| 3004 | THIRD TYPE | 15°C | 42°C |

70

FIG.16

| SCOPE ID | SCOPE TYPE | LOWEST TEMPERATURE | HIGHEST TEMPERATURE | AUTHORIZATION INFORMATION |
|---|---|---|---|---|
| 1001 | FIRST TYPE | 15.1°C | 42.1°C | PERMITTED |
| 1002 | FIRST TYPE | 14.8°C | 42°C | PERMITTED |
| 1003 | FIRST TYPE | 14.9°C | 41.9°C | PERMITTED |
| 1004 | FIRST TYPE | 15°C | 41.8°C | PERMITTED |
| 2001 | SECOND TYPE | 15°C | 42°C | NOT PERMITTED |
| 2002 | SECOND TYPE | 15°C | 42°C | NOT PERMITTED |
| 2003 | SECOND TYPE | 14.9°C | 41.8°C | NOT PERMITTED |
| 2004 | SECOND TYPE | 15°C | 42°C | NOT PERMITTED |
| 3001 | THIRD TYPE | 15°C | 42°C | PERMITTED |
| 3002 | THIRD TYPE | 15.1°C | 42.1°C | PERMITTED |
| 3003 | THIRD TYPE | 15.1°C | 42.1°C | PERMITTED |
| 3004 | THIRD TYPE | 15°C | 42°C | PERMITTED |

70

MEDICAL INSTRUMENT CONTROL SYSTEM, CONTROL DEVICE, MANAGEMENT SERVER, AND MEDICAL INSTRUMENT CONTROL METHOD

CROSS-REFERENCE TO RELATED APPLICATIONS

This application is based upon and claims the benefit of priority from the International Application No. PCT/JP2021/022748, filed on Jun. 15, 2021, the entire contents of which are incorporated herein by reference.

BACKGROUND

1. Field of the Disclosure

The present disclosure relates to a technology for managing the use of medical instruments.

2. Description of the Related Art

In order to ensure medical safety and infection prevention, there are medical instrument products that are designed to be used only once. Such products are called single-use medical instruments, and once those instruments are used in a medical facility, the instruments are collected by specialized business operators. In recent years, from the viewpoints of effective utilization of resources and reduction of medical waste, remanufacturing of used single-use medical instruments has been attracting attention, in which the manufacturer/distributor is responsible for disassembling, cleaning, replacing parts, reassembling, sterilizing, etc., so that the instruments can be used again.

The specification of U.S. patent Ser. No. 10/226,163 discloses a system for determining whether a single-use endoscope has been used or not, and if not, allowing for the activation of the endoscope. However, if the endoscope has been used, the system presents a message to the user indicating that the use of the endoscope is not authorized and does not activate the endoscope.

Single-use medical instruments are transported to a medical facility while being packaged in sterile packs and stored in storage. Medical workers open the sterilization packs immediately before use, remove the single-use medical instruments from the sterilization packs, and use the instruments directly for medical operations such as examinations and surgeries. Since medical instruments packaged in sterilization packs are assumed to remain sterilized until the time of use, no disinfection, cleaning, or other treatment is performed after the sterilization packs are opened.

SUMMARY

However, if a situation arises during transportation that makes it impossible to maintain the sterilized state of medical instruments, the use of the medical instruments is undesirable. The same applies to cases such as when medical instruments are damaged during transportation. Therefore, a mechanism is preferably established for confirming that the quality of medical instruments is ensured before using the medical instruments in a medical facility. In this background, a purpose of the present disclosure is to provide a technology for managing the use of medical instruments.

A medical instrument control system according to one embodiment of the present disclosure includes: an accommodating container accommodating a medical instrument; a sensor unit that acquires environmental information obtained at the time of transportation of the accommodating container; a recording unit that records the environmental information acquired by the sensor unit; and a control device that control functions of the medical instrument. The control device has a function restriction unit that restricts the functions of the medical instrument based on the environmental information recorded in the recording unit.

A control device according to another embodiment of the present disclosure is a control device that controls functions of a medical instrument and includes a function restriction unit that restricts the functions of the medical instrument based on environmental information obtained at the time of transportation of an accommodating container that accommodates the medical instrument.

A management server according to yet another embodiment of the present disclosure is a management server that is capable of communicating with a control device for a medical instrument and that includes: a communication unit that receives environmental information obtained at the time of transportation of an accommodating container that accommodates a medical instrument; a recording unit that records the received environmental information in association with identification information of the medical instrument; and an information provider that provides authorization information generated based on the environmental information associated with the identification information or the result of comparison between the environmental information and a predetermined threshold value when the information provider receives an inquiry regarding the medical instrument having the identification information from the control device.

A medical instrument control method according to still another embodiment of the present disclosure includes: acquiring environmental information obtained at the time of transportation of an accommodating container that accommodates a medical instrument; and restricting the functions of the medical instrument based on the environmental information associated with identification information of the medical instrument.

Optional combinations of the aforementioned constituting elements and implementations of the present disclosure in the form of methods, apparatuses, systems, recording mediums, and computer programs may also be practiced as additional modes of the present disclosure.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which:

FIG. 6 is a diagram showing examples of recording details in which scope IDs and environmental information are associated with each other;

FIG. 7 is a diagram showing examples of set environmental conditions related to temperature;

FIG. 8 is a diagram showing authorization information generated by an authorization information generation unit;

FIG. 11 is a diagram showing examples of recording details in which the sensor unit ID and a plurality of scope IDs are associated with each other;

FIG. 15 is a diagram showing examples of recording details in which scope IDs and environmental information are associated with each other;

FIG. 16 is a diagram showing authorization information generated by the authorization information generation unit.

DETAILED DESCRIPTION

The disclosure will now be described by reference to the preferred embodiments. This does not intend to limit the scope of the present disclosure, but to exemplify the disclosure.

Figure 1:
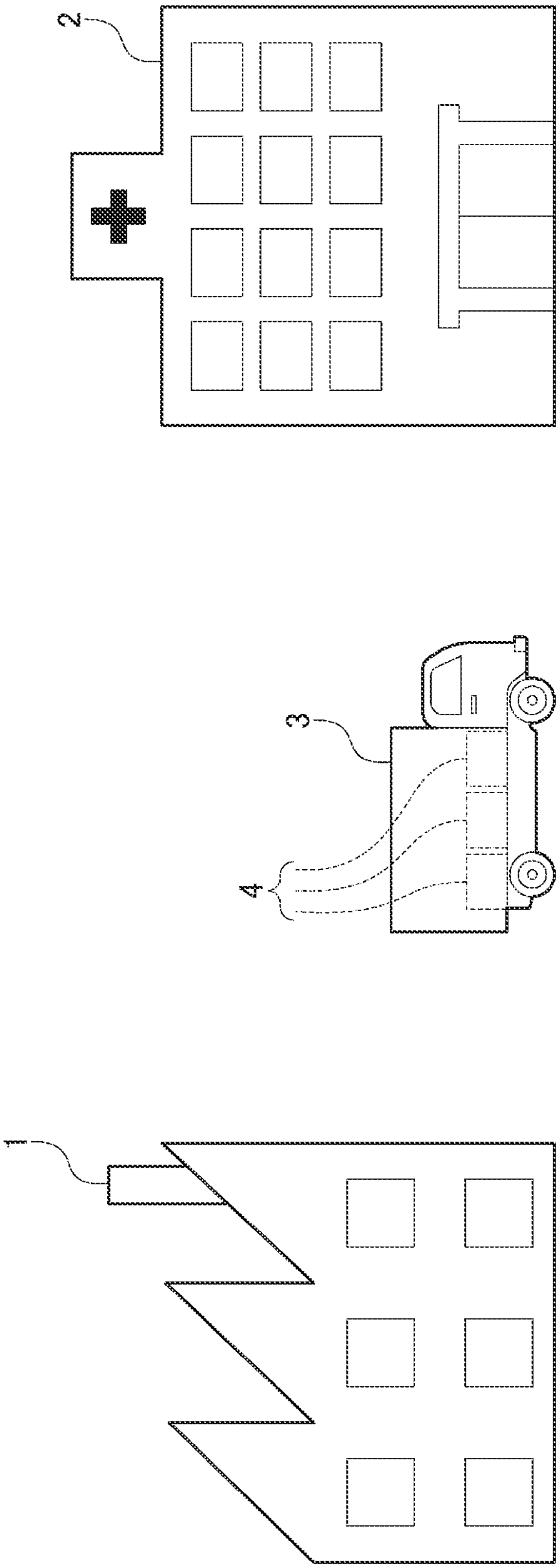
FIG. 1 is a diagram schematically showing the transportation of medical instruments.

FIG. 1 schematically shows the transportation of medical instruments. Medical instruments manufactured at a manufacturing facility 1 are individually packaged in sterilized packs, accommodated in accommodating containers 4, and then transported to a medical facility 2 by a transportation means 3, which is a moving body. Multiple medical instruments may be packed in one accommodating container 4. In the example shown in FIG. 1, the transportation means 3 is a truck. Alternatively, the transportation means 3 may include trains, railroads, air vehicles, ships, and the like, and the accommodating containers 4 may be transported from the manufacturing facility 1 to the medical facility 2 by multiple types of transportation means 3. The accommodating containers 4 may be brought from the manufacturing facility 1 to the medical facility 2 via a storage facility such as a warehouse. In an embodiment, medical instruments to be transported are single-use endoscopes. However, the medical instruments may be any single-use medical instruments other than endoscopes.

Environmental conditions suitable for transportation are set for medical instruments in order to guarantee their quality. The environmental conditions suitable for transportation are defined by the threshold values of environmental elements, and the quality of the medical instruments is guaranteed when the transportation means 3 transports the medical instruments in an environment where the threshold values are not exceeded. The threshold values of the environmental elements may be values set for the transportation of the medical instruments and appropriate values suitable for transportation, or the threshold values may be the appropriate values plus a margin. For example, if a lower temperature limit and an upper temperature limit are set as environmental conditions suitable for transportation, the transportation means 3 needs to maintain the temperature in the accommodating containers 4 accommodating medical instruments at a temperature that does not exceed (falls below) the lower limit and does not exceed (rises above) the upper limit. If the temperature inside the accommodating containers 4 deviates from the proper range defined by the lower and upper limits during transportation, a problem may occur such as deterioration of the seal of the sterilized packs.

Further, the medical instruments may be damaged if impact forces are applied to the medical instruments during transportation. Therefore, as environmental conditions for quality assurance, limit values for acceleration and/or deceleration applied to the medical instruments may be set, and the transportation means 3 needs to transport the medical instruments such that the acceleration and/or deceleration applied to the medical instruments does not exceed the limit values. Environmental elements that may affect the quality of the medical instruments during transportation include, for example, humidity, illumination, and atmospheric pressure, in addition to the temperature around the medical instruments and acceleration and/or deceleration applied to the medical instruments.

Figure 2:
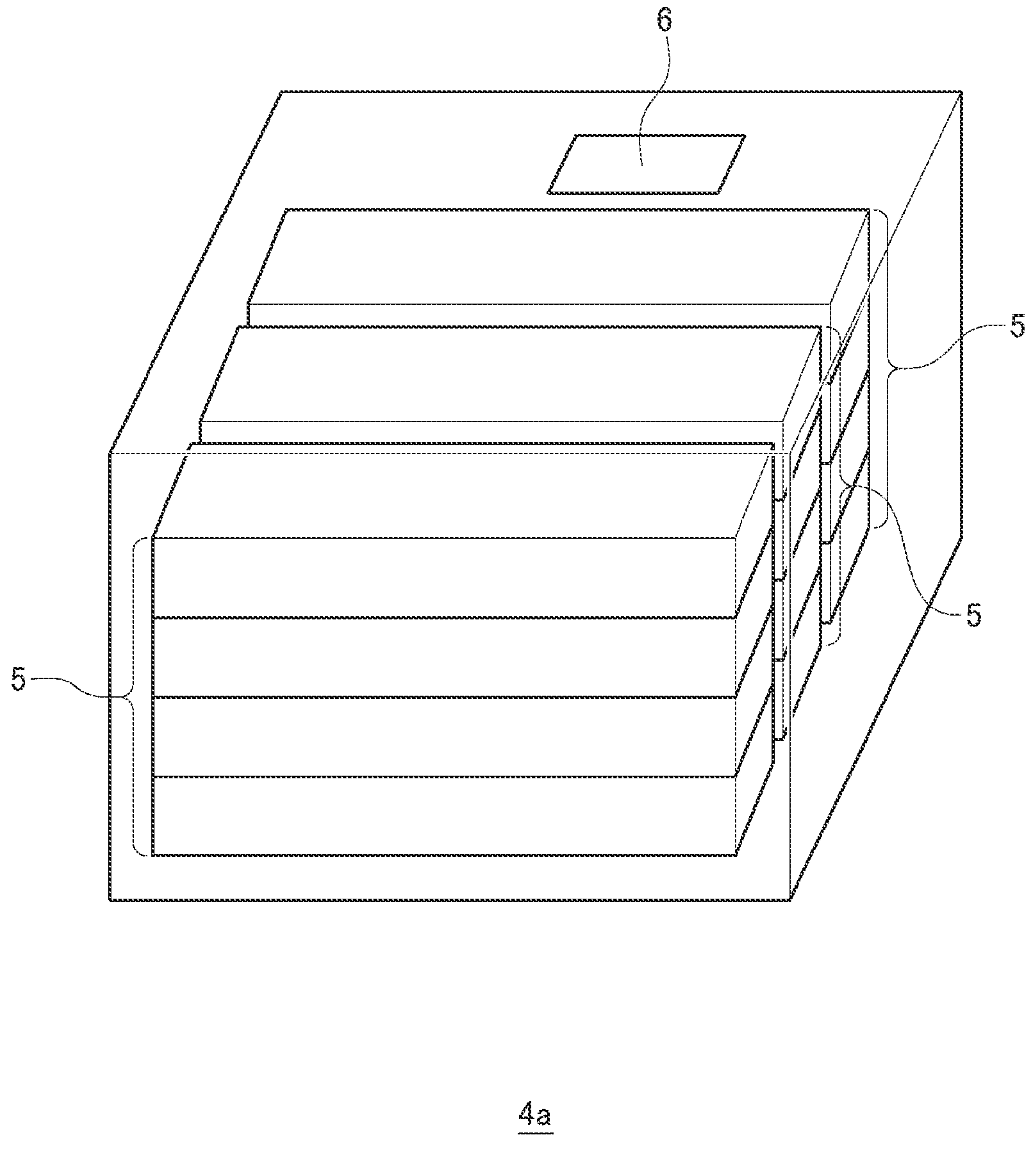
FIG. 2 is a diagram showing an example of an accommodating container.

FIG. 2 shows an example of an accommodating container 4*a* according to an embodiment. One or more individual packaging boxes 5 containing medical instruments are accommodated in the accommodating container 4*a* for transportation. Inside the individual packaging boxes 5, the medical instruments are in a state of being packaged in sterile packs. A plurality of individual packaging boxes 5 may be accommodated in an inner box, and one or more inner boxes may be accommodated in the accommodating container 4*a*.

A sensor unit 6 is provided in the accommodating container 4*a* and acquires environmental information obtained at the time of transportation of the accommodating container 4*a*. The environmental information acquired by the sensor unit 6 is detected values of environmental elements related to the environmental conditions suitable for transportation (hereinafter also referred to as "set environmental conditions"), and may include detected values of temperature, acceleration, deceleration, humidity, illumination, and atmospheric pressure.

Figure 3:
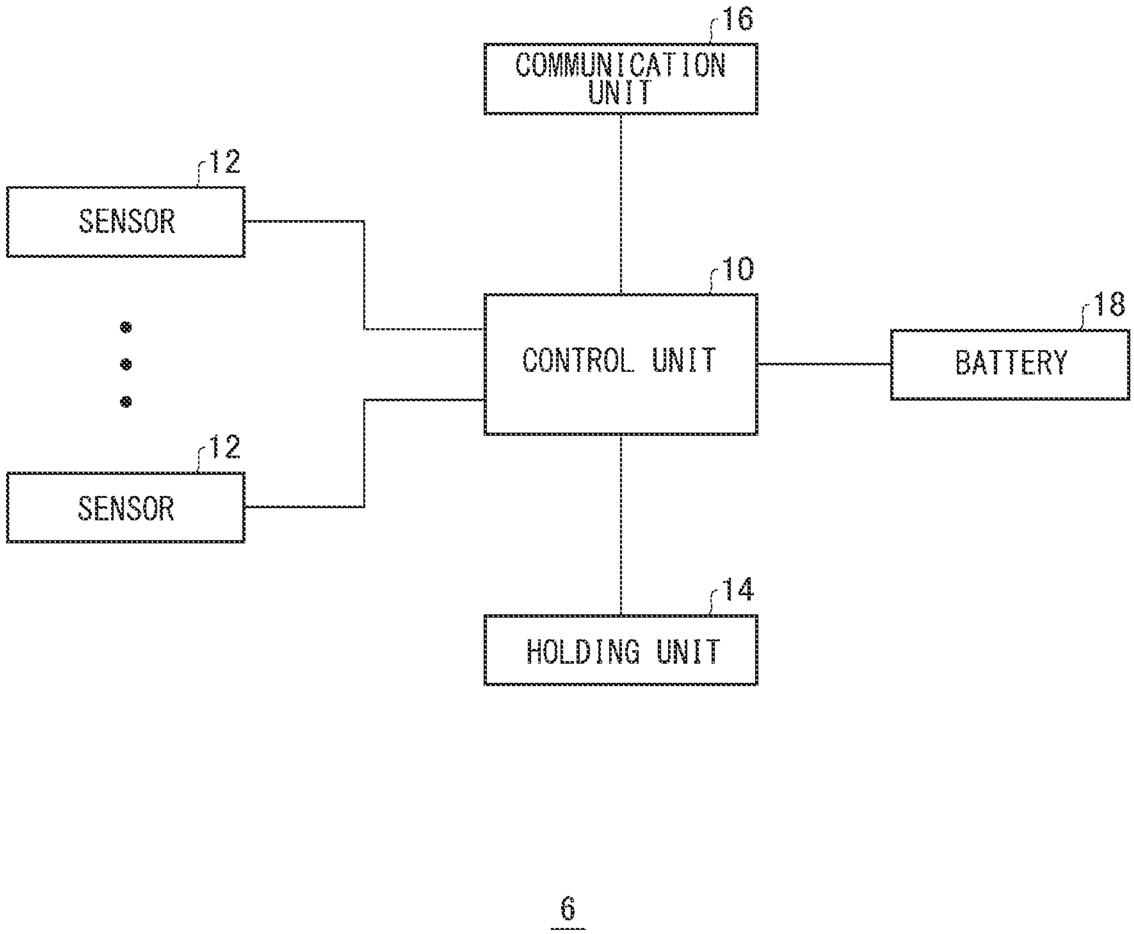
FIG. 3 is a diagram showing functional blocks of a sensor unit.

FIG. 3 shows functional blocks of the sensor unit 6. The sensor unit 6 includes a control unit 10 that manages the operation of the sensor unit 6, one or more sensors 12 that detect environmental information, a holding unit 14, a communication unit 16, and a battery 18. The battery 18 supplies power to each component in the sensor unit 6. The sensor unit 6 acquires environmental information until the accommodating containers 4 are transported out of the manufacturing facility 1 and arrive at the medical facility 2.

The configuration shown in FIG. 3 is implemented by hardware such as an arbitrary processor, memory, auxiliary storage, or other LSIs and by software such as a program or the like loaded into the memory. The figure depicts functional blocks implemented by the cooperation of hardware and software. Thus, a person skilled in the art should appreciate that there are many ways of accomplishing these functional blocks in various forms in accordance with the components of hardware only, software only, or the combination of both.

Each sensor 12 detects information regarding each environmental element, for example, temperature, acceleration, deceleration, humidity, illumination, and atmospheric pressure. The control unit 10 records the environmental information detected by the sensors 12 in the holding unit 14. The control unit 10 may record the environmental information along with detection time in the holding unit 14. At least one of the standard time of each of the departure, arrival, and transit locations may be selected, and the detection time may be recorded in the holding unit 14. The control unit 10 may record the periodically-detected environmental information in the holding unit 14 or may also record the minimum and/or maximum values of the environmental information for the purpose of reducing the amount of data to be recorded in the holding unit 14. For example, with respect to temperature, if the minimum temperature and the maximum temperature are recorded in the holding unit 14 as "15° C." and as "40° C.", respectively, when a sensor 12 detects a temperature lower than 15° C., the control unit 10 updates the minimum temperature and records the minimum temperature in the holding unit 14, and when a sensor 12 detects a temperature higher than 40° C., the control unit 10 updates the maximum temperature and records the maximum temperature in the holding unit 14. On the other hand, if the temperature detected by a sensor 12 is not less than the minimum temperature nor more than the maximum temperature recorded in the holding unit 14, the control unit does not record the detected temperature and may discard the information. By recording only the minimum and/or maximum values of environmental information in the holding unit 14 in this manner, the recording capacity that is used can be significantly reduced.

The holding unit 14 holds identification information of the medical instruments accommodated in the accommodating container 4*a*. For example, since twelve individual packaging boxes 5 containing medical instruments are accommodated in the accommodating container 4*a* in the example shown in FIG. 2, the identification information of the twelve medical instruments is recorded in the holding unit 14. Hereafter, the identification information of the medical instruments, which are endoscopes, is referred to as "scope ID".

Figure 4:
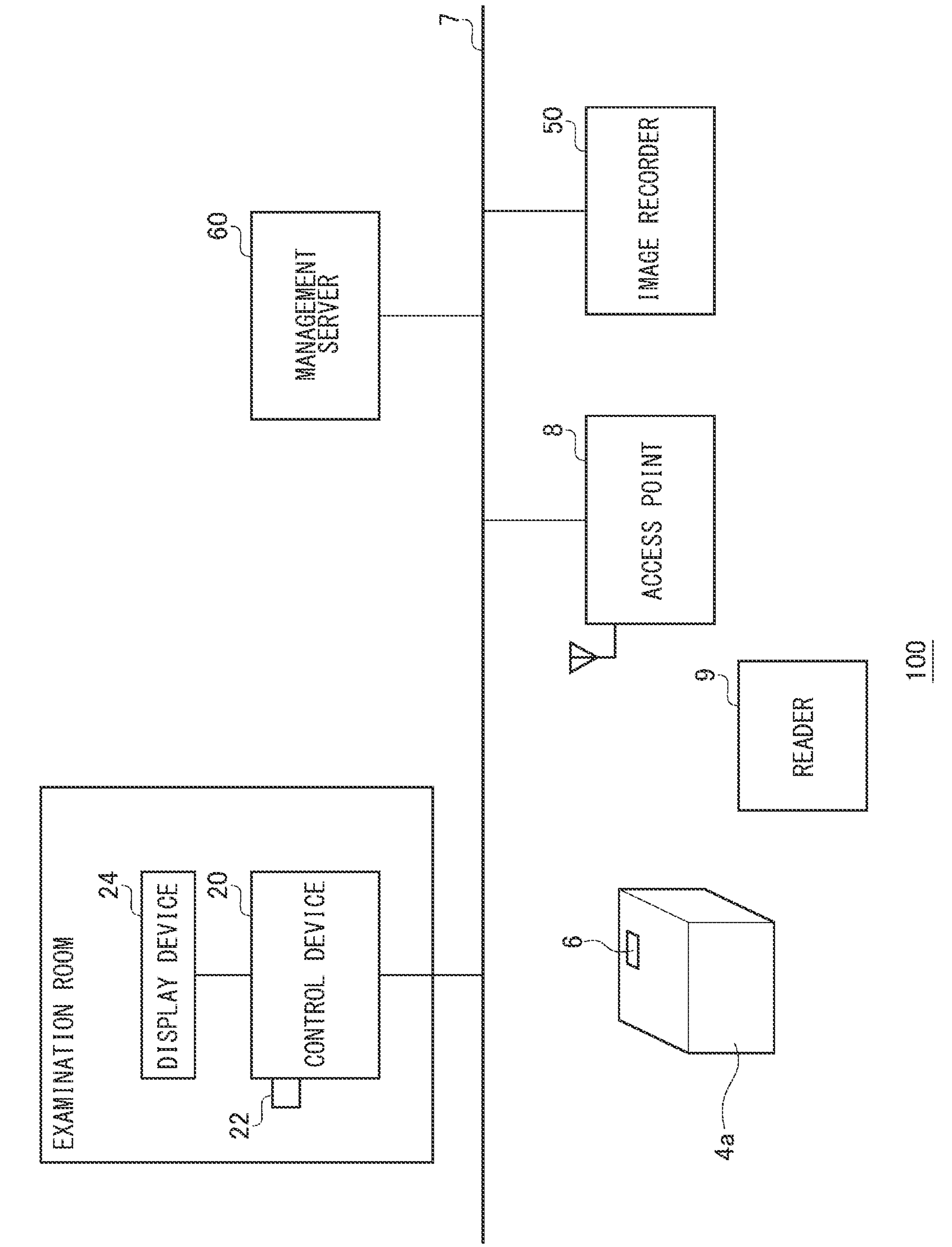
FIG. 4 is a diagram showing the configuration of a medical instrument control system.

FIG. 4 shows the configuration of a medical instrument control system 100 according to the embodiment. The medical instrument control system 100 is provided in the medical facility 2 and includes a control device 20, an image recorder 50, a management server 60, and an access point 8. The control device 20, the image recorder 50, the management server 60, and the access point 8 are communicatively connected by a network 7 such as a local area network (LAN).

The control device 20 is provided in an examination room. An endoscope, which is a medical instrument, is connected to a connection 22, and the control device 20 controls the functions of the endoscope. The control device 20 displays an image of the inside of a patient's body being captured by the endoscope on a display device 24, and the doctor observes each part of an organ that is displayed. When the doctor finds a lesion, the doctor operates a release switch of the endoscope so as to capture an image including the lesion. The control device 20 captures the image at the time when the release switch is operated and transmits the captured image to the image recorder 50. The control device 20 may transmit a plurality of captured images all at once to the image recorder 50 after the examination is completed.

The image recorder 50 is an image server that records images captured during an endoscopic examination and stores images transmitted from the control device 20 in association with an examination order. As metadata, the date and time of the image capturing, identification information of the endoscope (scope ID), information on the examination order, etc., may be added to a captured image. The control device 20 according to the embodiment controls the functions of the endoscope connected to the connection 22.

The following explains the process of storing endoscopes that are accommodated in the accommodating container 4*a* in storage. When the accommodating container 4*a* transported by the transportation means 3 is brought into the medical facility 2, a worker in the facility forwards the environmental information recorded in the sensor unit 6 to the management server 60. As shown in FIG. 3, if the sensor unit 6 is provided with a communication unit 16, the worker operates the sensor unit 6 so as to transmit the recorded environmental information to the management server 60. More specifically, when the worker inputs an instruction to the sensor unit 6 to transmit the environmental information, the control unit 10 reads the scope IDs of the plurality of endoscopes accommodated in the accommodating container 4*a* and the environmental information acquired during the transportation from the holding unit 14 and transmits the scope IDs and the environmental information through the communication unit 16 to the management server 60. The plurality of scope IDs and the environmental information may be transmitted to the management server 60 via the access point 8.

The worker may use the reader 9 to read the plurality of scope IDs and the environmental information from the sensor unit 6. Upon reading the plurality of scope IDs and the environmental information from the sensor unit 6, the reader 9 transmits the read plurality of scope IDs and environmental information to the management server 60. The plurality of scope IDs and the environmental information may be transmitted to the management server 60 via the access point 8. The sensor unit 6 may have a function of transmitting the recorded environmental information to the management server 60 via the Internet from the communication unit 16. In this case, the sensor unit 6 may transmit the recorded environmental information to the management server 60 during transportation or upon arrival at the medical facility 2.

Figure 5:
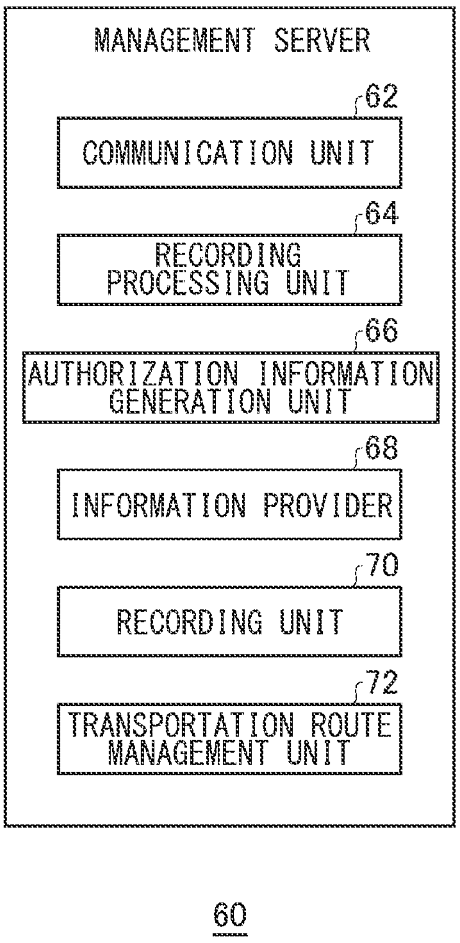
FIG. 5 is a diagram showing functional blocks of a management server.

FIG. 5 shows functional blocks of the management server 60. The management server 60 includes a communication unit 62, a recording processing unit 64, an authorization information generation unit 66, an information provider 68, a recording unit 70, and a transportation route management unit 72. The configuration shown in FIG. 5 is implemented by hardware such as an arbitrary processor, memory, auxiliary storage, or other LSIs and by software such as a program or the like loaded into the memory. The figure depicts functional blocks implemented by the cooperation of hardware and software. Thus, a person skilled in the art should appreciate that there are many ways of accomplishing these functional blocks in various forms in accordance with the components of hardware only, software only, or the combination of both.

The communication unit 62 receives the plurality of scope IDs and the environmental information from the sensor unit 6. As described above, the plurality of scope IDs are identification information of the plurality of endoscopes accommodated in one accommodating container 4*a*, and the environmental information is environmental information acquired by the sensor unit 6 at the time of transportation of the accommodating container 4*a*. The recording processing unit 64 records the environmental information acquired by the sensor unit 6 in the recording unit 70. At this time, the recording processing unit 64 records the environmental information in the recording unit 70 in association with the identification information of the medical instruments (i.e., the scope IDs of the endoscopes).

FIG. 6 shows examples of recording details in which scope IDs and environmental information obtained at the time of transportation are associated with each other. In the example shown in FIG. 6, the minimum and maximum temperatures acquired by the sensor 12 are recorded in the recording unit 70 as environmental information obtained at the time of transportation. Alternatively, information detected on other environmental elements such as acceleration, deceleration, humidity, illumination, and atmospheric pressure may be recorded in the recording unit 70.

Three types of endoscopes are accommodated in the transported accommodating container 4A. In this example, endoscopes with scope IDs of "1001", "1002", "1003", and "1004" are denoted as "first type endoscopes", endoscopes with scope IDs of "2001", "2002", "2003", and "2004" are denoted as "second type endoscopes", endoscopes with scope IDs of "3001", "3002", "3003", and "3004" are denoted as "third type endoscopes".

As described above, for the purpose of guaranteeing the quality of medical instruments after transportation, predetermined threshold values are set for environmental elements obtained at the time of transportation for the medical instruments. The threshold values are set to such values that a malfunction of the medical instruments may be caused if the values of the environmental elements exceed the threshold values at the time of transportation of the medical instruments. Therefore, medical instruments with environmental elements whose values have exceeded the threshold values at the time of transportation need to be prohibited from being used in the medical facility 2.

The threshold values of environmental elements (set environmental conditions) at the time of transportation are set by the manufacturer for each medical instrument type. As for endoscopes, there are various types of endoscopes such as otorhinolaryngological scopes, bronchoscopes, upper gastrointestinal general-purpose scopes, duodenal scopes, and colonoscopes, and the threshold values of environmental elements at the time of transportation may be set for each endoscope type. The threshold values of the environmental elements at the time of transportation (set environmental conditions) may be set for each endoscope model number.

FIG. 7 shows examples of set environmental conditions for temperature set for each endoscope type. The set environmental conditions are managed by the authorization information generation unit 66. The lower and upper temperature limits for the first type endoscopes are set to 0° C. and 50° C., respectively. These set environmental conditions mean that the quality of the first type endoscopes cannot be guaranteed if the temperature at the time of transportation falls below 0° C. or rises above 50° C. The lower and upper temperature limits of the set environmental conditions may each be a temperature set as a defined value or may each be a temperature obtained by changing the defined value by a predetermined value. The lower and upper temperature limits of the second type endoscopes are set at 0° C. and 40° C., respectively, while the lower and upper temperature limits of the third type endoscopes are set at −30° C. and 50° C., respectively.

When environmental information associated with scope IDs is recorded in the recording unit 70, the authorization information generation unit 66 compares the environmental information with the set environmental conditions and generates authorization information indicating whether the endoscopes are permitted or prohibited to be used based on the comparison results.

Referring to the recording details from the recording unit 70 shown in FIG. 6, the first type endoscopes with the scope IDs of "1001", "1002", "1003", and "1004" have been transported in an environment with a minimum temperature of 15° C. and a maximum temperature of 42° C. Since the minimum temperature (15° C.) and maximum temperature (42° C.) are within the proper range of the set environmental conditions for the first type endoscopes shown in FIG. 7, the authorization information generation unit 66 determines that the first type endoscopes with the scope IDs of "1001", "1002", "1003", and "1004" have been properly transported and therefore decides to permit the use of the endoscopes.

The minimum temperature (15° C.) and maximum temperature (42° C.) at the time of transportation of the third type endoscopes with IDs "3001", "3002", "3003", and "3004" are also within the proper range of the set environmental conditions for the third type endoscopes shown in FIG. 7. Accordingly, the authorization information generation unit 66 determines that the third type endoscopes with the scope IDs of "3001", "3002", "3003", and "3004" have been properly transported and therefore decides to permit the use of the endoscopes.

On the other hand, although the minimum temperature (15° C.) at the time of transportation of the second type endoscopes with IDs "2001", "2002", "2003", and "2004" is within the proper range of the set environmental conditions for the second type endoscopes shown in FIG. 7, the maximum temperature (42° C.) falls outside the proper range of the set environmental conditions and exceeds the upper temperature limit (40° C.). Accordingly, the authorization information generation unit 66 determines that the second type endoscopes with the scope IDs of "2001", "2002", "2002", and "2004" have been improperly transported and therefore decides to prohibit the use of the endoscopes.

FIG. 8 shows authorization information generated by the authorization information generation unit 66. The authorization information generation unit 66 generates non-permission information indicating that the use of endoscopes is not permitted when the environmental information at the time of transportation exceeds predetermined threshold values defined by the set environmental conditions. The non-permission information may be referred to as use prohibition information. On the other hand, the authorization information generation unit 66 generates permission information indicating that the use of endoscopes is permitted when the environmental information at the time of transportation does not exceed the predetermined threshold values defined by the set environmental conditions. The recording processing unit 64 records the authorization information generated by the authorization information generation unit 66 in the recording unit 70 in association with the scope IDs.

After the scope IDs and the environmental information are read out from the sensor unit 6, the accommodating container 4*a* brought into the medical facility 2 is opened and the individual packaging boxes 5 are taken out. The worker stores the taken-out individual packaging boxes 5 in the storage. The accommodating container 4*a* may be returned to the manufacturing facility 1.

Figures 9, 10:
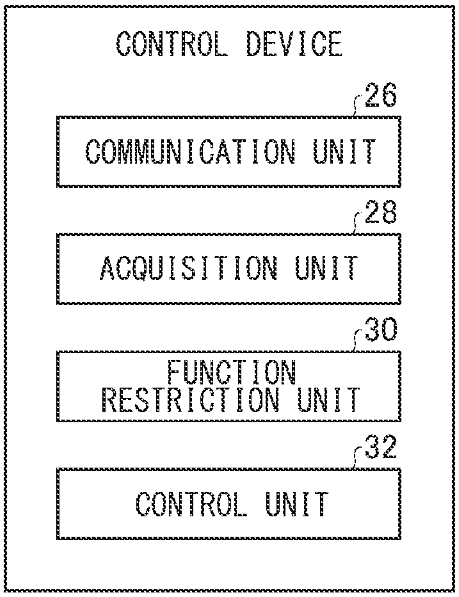
FIG. 9 is a diagram showing functional blocks of a control device.
FIG. 10 is a diagram showing examples of recording details in which a sensor unit ID and environmental information are associated with each other.

A process for taking out an endoscope from an individual packaging box 5 and using the endoscope for an endoscopic examination will be explained below. FIG. 9 shows functional blocks of the control device 20. The control device 20 has a communication unit 26, an acquisition unit 28, a function restriction unit 30, and a control unit 32. The configuration shown in FIG. 9 is implemented by hardware such as an arbitrary processor, memory, auxiliary storage, or other LSIs and by software such as a program or the like loaded into the memory. The figure depicts functional blocks implemented by the cooperation of hardware and software. Thus, a person skilled in the art should appreciate that there are many ways of accomplishing these functional blocks in various forms in accordance with the components of hardware only, software only, or the combination of both.

Before the start of the endoscopic examination, a medical worker such as a nurse takes out an individual packaging box 5 from the storage and brings the individual packaging box 5 to an examination room. The medical worker opens the individual packaging box 5, takes out an endoscope packaged in a sterilization pack, opens the sterilization pack, and takes out the endoscope from the sterilization pack.

The medical worker connects the endoscope taken out from the sterilization pack to the connection 22 of the control device 20. At this point, the endoscope connected to the connection 22 is an endoscope that is scheduled to be used for the endoscopic examination, and it has not been confirmed that the endoscope can be used. When the endoscope is connected to the connection 22, the acquisition unit 28 acquires the scope ID, which is the identification information of the endoscope, from the endoscope. At this time, the function restriction unit 30 has a function of restricting the functions of the endoscope based on the environmental information recorded in the recording unit 70 in the management server 60. More specifically, the function restriction unit 30 has a function of restricting the functions of the endoscope based on the authorization information generated based on the result of comparison between the environmental information associated with the scope ID and a predetermined threshold value.

Referring to FIG. 8, when the scope ID of the endoscope connected to the connection 22 is "2002", the function restriction unit 30 makes an inquiry to the management server 60 for the authorization information of the scope ID "2002". Upon receiving the inquiry, the information provider 68 in the management server 60 searches the recording unit 70 to read the authorization information associated with the scope ID "2002" and provides the authorization information (non-permission information) indicating that the use of the endoscope is not permitted to the control device 20 from the communication unit 62. In the control device 20, the communication unit 26 receives the authorization information indicating the non-permission to use the endoscope, and the function restriction unit 30 restricts the functions of the endoscope.

The function restriction unit 30 restricts the functions of the endoscope such that medical workers cannot practically use the endoscope. For example, the function restriction unit 30 may stop the power supply to the endoscope so as do disable the image capturing of the inside of the body of the patient. Alternatively, without restricting the image capturing by a camera, the function restriction unit 30 may stop the power supply to the display device 24 such that captured images cannot be displayed. The function restriction unit 30 may blur or partially hide a captured image displayed on the display device 24 or display a message on the captured image indicating that the endoscope cannot be used, thereby practically preventing the medical worker from using the endoscope. By restricting the functions of an endoscope in this manner, the function restriction unit 30 can practically prohibit the use of the endoscope that has been transported in an inappropriate environment.

On the other hand, when the scope ID of the endoscope connected to the connection 22 is "1002", the function restriction unit 30 makes an inquiry to the management server 60 for the authorization information of the scope ID "1002", and the information provider 68 in the management server 60 reads the authorization information associated with the scope ID "1002" from the recording unit 70 and provides the authorization information (permission information) indicating the use of the endoscope is permitted to the control device 20 from the communication unit 62. In the control device 20, when the communication unit 26 receives the permission information from the management server 60, the function restriction unit 30 does not restrict the functions of the endoscope, and the control unit 32 displays the images captured by the endoscope on the display device 24 such that the doctor observes the images displayed on the display device 24.

In the embodiment, it is explained that the authorization information generation unit 66 generates the authorization information when the environmental information is recorded in the recording unit 70. Alternatively, the authorization information generation unit 66 may generate the authorization information at the time when an inquiry for the authorization information is received from the control device 20. In the embodiment, it is also explained that the function restriction unit 30 implements the function restriction of an endoscope based on the authorization information recorded in the recording unit 70.

Alternatively, the information provider 68 may provide the environmental information recorded in the recording unit 70 to the control device 20, and the function restriction unit may determine whether the use of the endoscope is permitted or not based on the environmental information and then implement the function restriction of the endoscope.

<First Exemplary Variation>

In the above embodiment, it is assumed that the scope ID of an endoscope accommodated in the accommodating container 4*a* is held in the holding unit 14 of the sensor unit 6. However, in the first exemplary variation, the scope ID of an endoscope accommodated in the accommodating container 4*a* is associated with the identification information of the sensor unit 6 and managed by the management server 60.

In the first exemplary variation, instead of the scope ID, the identification information (sensor unit ID) of the sensor unit 6 is held in the holding unit of the sensor unit 6. When the accommodating container 4*a* accommodating endoscopes is transported to the medical facility 2, a worker in the facility inputs an instruction to the sensor unit 6 to transmit the environmental information, and the control unit reads the sensor unit ID and the environmental information acquired during transportation from the holding unit 14 and transmits the sensor unit ID and the environmental information to the management server 60 through the communication unit 16.

In the management server 60, the communication unit 62 receives the sensor unit ID and the environmental information. The recording processing unit 64 records the environmental information in the recording unit 70 by associating the environmental information with the sensor unit ID.

FIG. 10 shows examples of recording details in which the sensor unit ID and the environmental information at the time of transportation are associated with each other. In the example shown in FIG. 10, the minimum and maximum temperatures acquired by the sensor 12 are recorded in the recording unit 70 as environmental information at the time of transportation. Alternatively, information detected on other environmental elements such as acceleration, deceleration, humidity, illumination, and atmospheric pressure may be recorded in the recording unit 70.

FIG. 11 shows examples of recording details in which the sensor unit ID and a plurality of scope IDs are associated with each other. The management server 60 acquires from the manufacturing facility 1 the combination of the sensor unit ID of the sensor unit 6 provided in the accommodating container 4*a* and the scope IDs of the endoscopes accommodated in the accommodating container 4*a*, and the recording processing unit 64 records the combination in the recording unit 70. In this manner, in first exemplary variation, the recording unit 70 may record the scope IDs and the environmental information in association with the sensor unit ID.

<Second Exemplary Variation>

Figure 12:
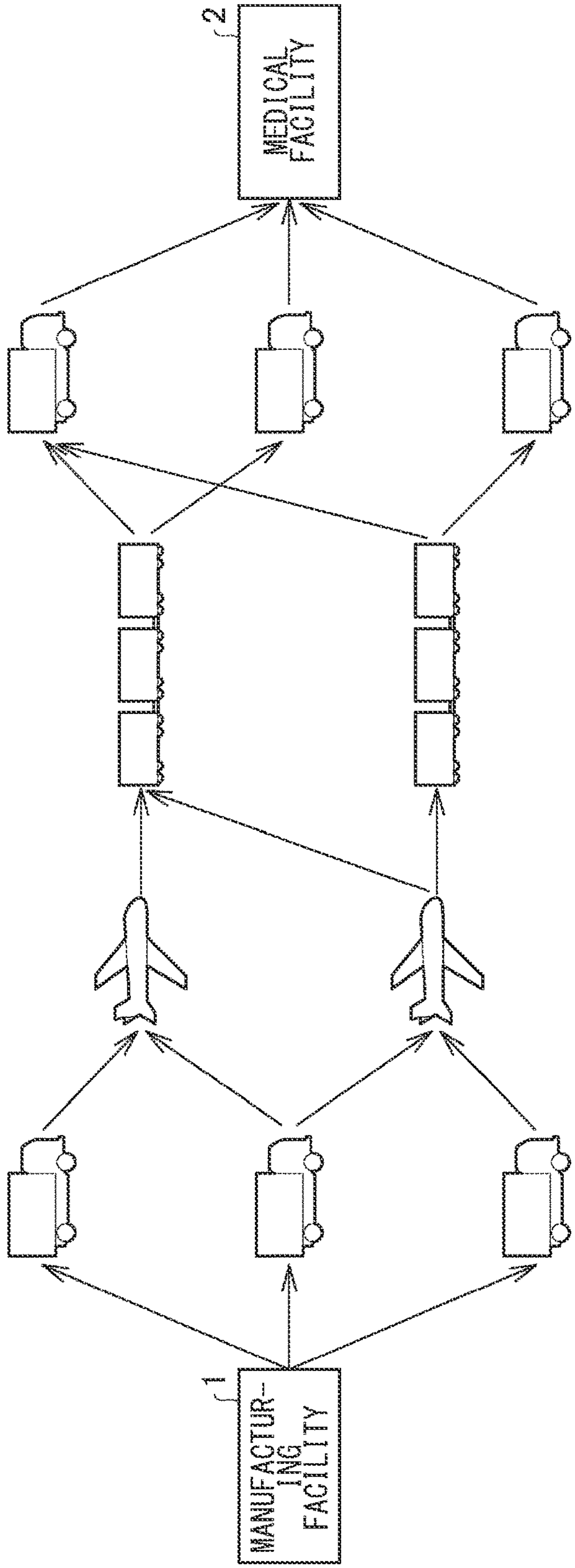
FIG. 12 shows an example of a transportation route from a manufacturing facility to a medical facility.

In the second exemplary variation, the process of prohibiting the use of medical instruments is shown while focusing on the transportation route of the accommodating container 4*a*. FIG. 12 shows an example of a transportation route from the manufacturing facility 1 to the medical facility 2. Accommodating containers 4*a* are transported from the manufacturing facility 1 to the medical facility 2 by various types of transportation means 3.

The transportation route management unit 72 manages the transportation route of all the accommodating containers 4*a* to be transported. The transportation route in this case is defined by at least one of the transportation means 3 and the course, and the same transportation route means that at least one of the transportation means 3 and the course is the same. The transportation route management unit 72 keeps track of the identification information of the transportation means 3 used for transportation and the transportation time (transportation start time and transportation completion time) by the transportation means 3 for all the accommodating containers 4*a*. For example, if the accommodating containers 4*a* are transported by multiple transportation means 3, the transportation route management unit 72 records the identification information of each transportation means 3 and the transportation time. In the sensor unit 6 according to the second exemplary variation, the control unit 10 records the time when the value of an environmental element exceeds a predetermined threshold value in the holding unit 14 along with the environmental element value.

For example, a case is assumed where out of ten accommodating containers 4*a* transported in the same aircraft, acceleration values acquired by sensor units 6 provided in nine accommodating containers 4*a* exceed a predetermined threshold value defined by the set environmental condition and an acceleration value acquired by a sensor unit 6 provided in one accommodating container 4*a* is below the predetermined threshold value. In air transportation, when an aircraft is caught in turbulence, acceleration values detected by sensor units 6 show large values. Therefore, if the factor that caused a detected acceleration value to exceed the value according to the set environmental condition is turbulence, it is highly likely that sensor units 6 that showed proper acceleration values are out of order.

Therefore, the transportation route management unit 72 identifies a transportation route used when the value of an environmental element acquired by a sensor unit 6 provided in a first accommodating container 4*a* exceeds the predetermined threshold value and identifies a second accommodating container 4*a* transported on the same transportation route as the identified transportation route. Based on the time recorded in the sensor unit 6 provided in the first accommodating container 4*a* (the time when the value of the environmental element exceeded the predetermined threshold value), the transportation route management unit 72 identifies a transportation means 3 used for transportation at that time and identifies the second accommodating container 4*a* being transported by the same transportation means 3 at that time. The authorization information generation unit 66 generates authorization information indicating that the use of the medical instrument accommodated in the second accommodating container 4*a* is not permitted, even if the value of the environmental element acquired by the sensor unit 6 provided in the second accommodating container 4*a* does not exceed the predetermined threshold value. The authorization information generation unit 66 may generate authorization information that indicates that the use of the medical instrument accommodated in the second accommodating container 4*a* is not permitted on the condition that environmental element values acquired by the respective sensor units 6 of half of the multiple accommodating containers 4*a* or more transported by the same transportation means 3 exceed the predetermined threshold value. According to the second exemplary variation, even if the sensor unit 6 of the second accommodating container 4*a* is out of order, the use of the medical instrument can be prohibited on the presumption that there is a possibility that the medical instrument is malfunctioning.

<Third Exemplary Variation>

Figure 13:
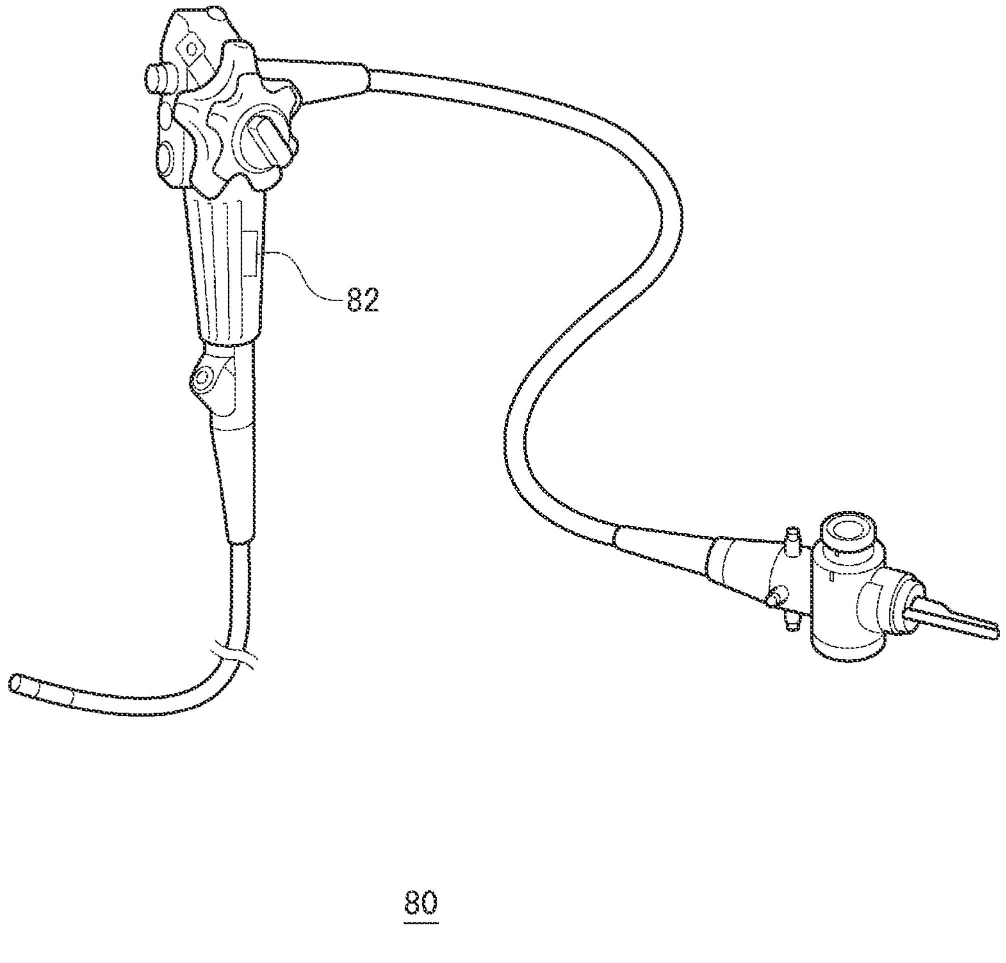
FIG. 13 is a diagram showing an example of an endoscope.

In the third exemplary variation, a recording unit that records environmental information acquired by a sensor unit 6 is provided in a medical instrument. FIG. 13 shows an example of an endoscope 80 that is transported while being accommodated in an accommodating container 4*a*. A recording unit 82 for recording environmental information acquired by a sensor unit 6 is provided in an endoscope 80. The scope ID, which is the identification information of the endoscope 80, is recorded in the recording unit 82. The recording unit 82 may be an RF tag, and the sensor unit 6 may function as a reader/writer for the recording unit 82, which is an RF tag.

In the third exemplary variation, when a worker in a medical facility takes out an individual packaging box 5 from an accommodating container 4*a*, the worker brings the individual packaging box 5 close to the sensor unit 6 so as to thereby record the environmental information recorded in the sensor unit 6 in the recording unit 82. An RFID reader/writer may be arranged for individual packaging boxes such that environmental information acquired by sensor unit 6 is recorded in the recording unit 82 in the accommodating container 4*a* even when the worker does not bring individual packaging boxes 5 close to the sensor unit 6. The worker stores the individual packaging boxes 5 with the environmental information recorded in the recording unit 82 in the storage.

A process for taking out an endoscope 80 from an individual packaging box 5 and using the endoscope for an endoscopic examination will be explained below. Before the start of the endoscopic examination, a medical worker brings an individual packaging box 5 to an examination room from the storage. The medical worker opens the individual packaging box 5, takes out a sterilization pack in which an endoscope 80 is packaged, opens the sterilization pack, takes out the endoscope 80 from the sterilization pack, and connects the endoscope 80 to the connection 22 of the control device 20. The acquisition unit 28 acquires from the endoscope 80 the scope ID, which is the identification information of the endoscope 80, and environmental information at the time of transportation.

In the third exemplary variation, the acquisition unit 28 may further have an RFID reader/writer function and read at least the environmental information recorded in the recording unit 82 of the endoscope 80 by the RFID reader function.

The function restriction unit 30 determines whether or not to restrict the functions of the endoscope 80 based on the scope ID and the environmental information. More specifically, the function restriction unit 30 makes an inquiry to the management server 60 for set environmental conditions that are set for the acquired scope ID and acquires the set environmental conditions. The set environment conditions may be recorded in the recording unit 82 of the endoscope 80, or the acquisition unit 28 may acquire the set environment conditions from the recording unit 82. The function restriction unit 30 compares the environmental information obtained at the time of transportation with the set environmental conditions. If the environmental information at the time of transportation does not exceed predetermined threshold values of the set environmental conditions, the function restriction unit 30 determines that the use of the endoscope 80 is permitted and does not restrict the functions of the endoscope 80. On the other hand, if the environmental information at the time of transportation exceeds the predetermined thresholds of the set environmental conditions, the function restriction unit determines that the use of the endoscope 80 is prohibited and restricts the functions of the endoscope 80.

<Fourth Exemplary Variation>

Figure 14:
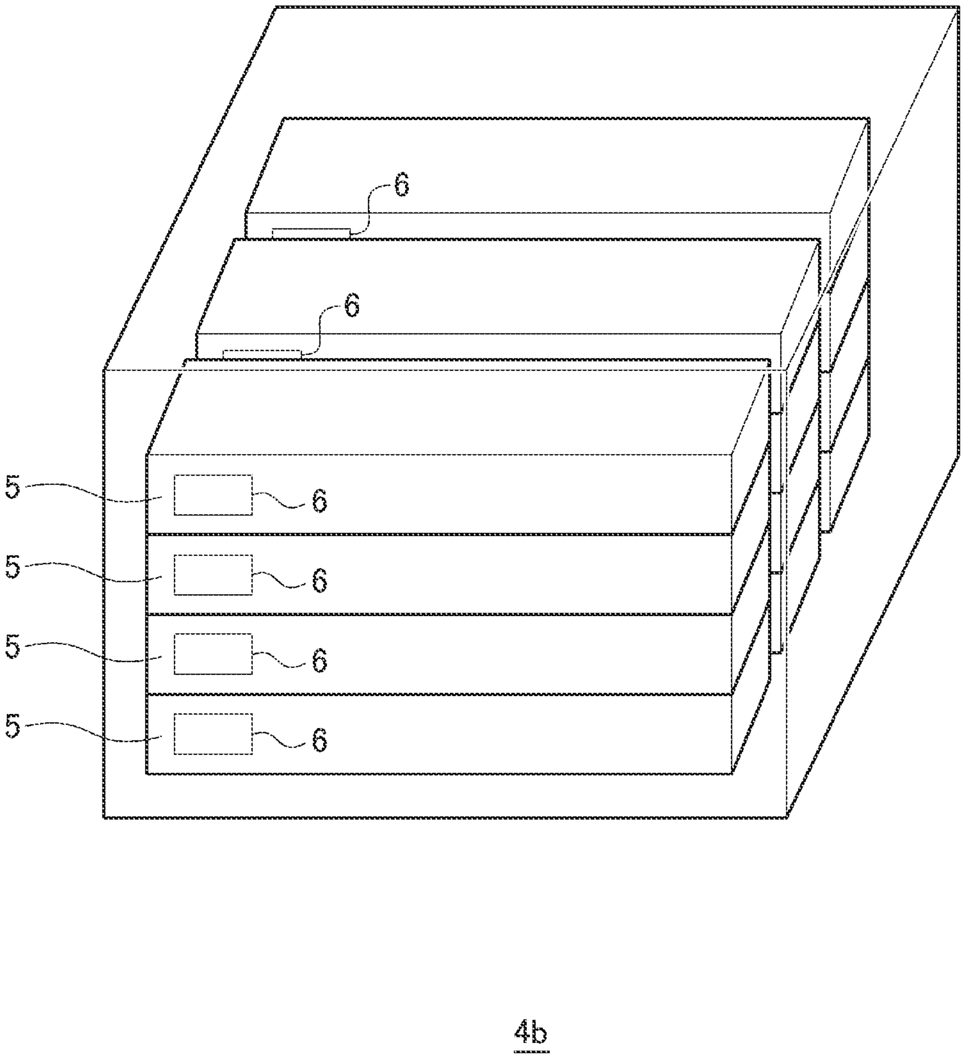
FIG. 14 is a diagram showing an example of an accommodating container.

In the fourth exemplary variation, a sensor unit 6 is provided for each medical instrument. FIG. 14 shows an example of an accommodating container 4*b*. One or more individual packaging boxes 5 containing medical instruments are accommodated in the accommodating container 4*b* for transportation. Inside the individual packaging boxes 5, the medical instruments are in a state of being packaged in sterile packs. A plurality of individual packaging boxes 5 may be accommodated in an inner box, and one or more inner boxes may be accommodated in the accommodating container 4*b*.

In the fourth exemplary variation, a sensor unit 6 is provided in an individual packaging box 5. In other words, one sensor unit 6 is provided for one medical instrument so as to acquire environmental information obtained at the time of transportation of the individual packaging box 5. The environmental information acquired by the sensor unit 6 is detected values of environmental elements related to set environmental conditions and may include detected values of temperature, acceleration, deceleration, humidity, illumination, and atmospheric pressure. Since the individual packaging box 5 accommodates a medical instrument, the individual packaging box 5 may be referred to as "accommodating container".

The following explains the process of storing endoscopes that are accommodated in the accommodating container 4*b* in storage. When the accommodating container 4*b* accommodating endoscopes is brought into the medical facility 2, a worker in the facility opens the accommodating container 4*b* and takes out individual packaging boxes 5 that are accommodated. The worker transfers environmental information recorded in a sensor unit 6 attached to each individual packaging box 5 to the management server 60. As shown in FIG. 3, if the sensor unit 6 is provided with a communication unit 16, the worker operates the sensor unit 6 so as to transmit the recorded scope ID and environmental information to the management server 60. The worker may use a reader 9 to read the scope ID and the environmental information from the sensor unit 6. Upon reading the scope ID and the environmental information, the reader 9 transmits the read scope ID and environmental information to the management server 60. After transferring the scope IDs and environmental information recorded in all sensor units 6 to the management server 60, the worker stores the individual packaging boxes 5 in the storage. The accommodating container 4*a* may be returned to the manufacturing facility 1.

In the management server 60, the communication unit 62 receives multiple combinations of scope IDs and environmental information from the sensor units 6 or the reader 9. The recording processing unit 64 records the environmental information acquired by the sensor units 6 in the recording unit 70 in association with the identification information of the medical instruments (i.e., the scope IDs of the endoscopes).

FIG. 15 shows examples of recording details in which scope IDs and environmental information obtained at the time of transportation are associated with each other. In the example shown in FIG. 15, the minimum and maximum temperatures acquired by the sensor 12 are recorded in the recording unit 70 as environmental information obtained at the time of transportation. Alternatively, information detected on other environmental elements such as acceleration, deceleration, humidity, illumination, and atmospheric pressure may be recorded in the recording unit 70.

Compared to the recording details shown in FIG. 6, in the fourth exemplary variation, since the minimum and maximum temperatures acquired by a sensor unit 6 provided for each endoscope are recorded in the recording unit 70, the values are slightly different for each endoscope. In the fourth exemplary variation, the authorization information generation unit 66 compares environmental information for each endoscope with set environmental conditions and generates authorization information indicating whether the use of the endoscope is permitted or prohibited based on the comparison results.

FIG. 16 shows authorization information generated by the authorization information generation unit 66. The authorization information generation unit 66 generates non-permission information indicating that the use of endoscopes is not permitted when the environmental information at the time of transportation exceeds predetermined threshold values defined by the set environmental conditions. On the other hand, the authorization information generation unit 66 generates permission information indicating that the use of endoscopes is permitted when the environmental information at the time of transportation does not exceed the predetermined threshold values defined by the set environmental conditions. The recording processing unit 64 records the authorization information generated by the authorization information generation unit 66 in the recording unit 70 in association with the scope IDs.

<Fifth Exemplary Variation>

In the fifth exemplary variation, the process of prohibiting the use of medical instruments is shown while focusing on the transportation route of individual packaging boxes 5 on the assumption that a sensor unit 6 is provided for each medical instrument as explained in the fourth exemplary variation. The transportation route management unit 72 manages the transportation route of all individual packaging boxes 5 to be transported. The transportation route in this case is defined by at least one of the transportation means 3 and the course, and the same transportation route means that at least one of the transportation means 3 and the course is the same. The transportation route management unit 72 keeps track of the identification information of the transportation means 3 used for transportation and the transportation time (transportation start time and transportation completion time) by the transportation means 3 for all the individual packaging boxes 5. For example, if the individual packaging boxes 5 are transported by multiple transportation means 3, the transportation route management unit 72 records the identification information of each transportation means 3 and the transportation time. In the sensor unit 6 according to the fifth exemplary variation, the control unit 10 records the time when the value of an environmental element exceeds a predetermined threshold value in the holding unit 14 along with the environmental element value.

The transportation route management unit 72 identifies a transportation route used when the value of an environmental element acquired by a sensor unit 6 provided in a first individual packaging box 5 exceeds the predetermined threshold value and identifies a second individual packaging box 5 transported on the same transportation route as the identified transportation route. Based on the time recorded in the sensor unit 6 provided in the first individual packaging box 5 (the time when the value of the environmental element exceeded the predetermined threshold value), the transportation route management unit 72 identifies a transportation means 3 used for transportation at that time and identifies the second individual packaging box 5 being transported by the same transportation means 3 at that time. The authorization information generation unit 66 generates authorization information indicating that the use of the medical instrument accommodated in the second individual packaging box 5 is not permitted, even if the value of the environmental element acquired by the sensor unit 6 provided in the second individual packaging box 5 does not exceed the predetermined threshold value.

Described above is an explanation on the present disclosure based on the embodiments and the exemplary variations. These embodiments and exemplary variations are intended to be illustrative only, and it will be obvious to those skilled in the art that various modifications to constituting elements and processes could be developed and that other modifications are also within the scope of the present disclosure. In the embodiments, it is assumed that medical instruments are single-use medical instruments. Alternatively, the medical instruments may be reusable medical instruments for loan, which are loaned from the manufacturing facility 1 to the medical facility 2 and returned to the manufacturing facility 1 after being used in the medical facility 2 or may be simple reusable medical instruments.

Figure 17:
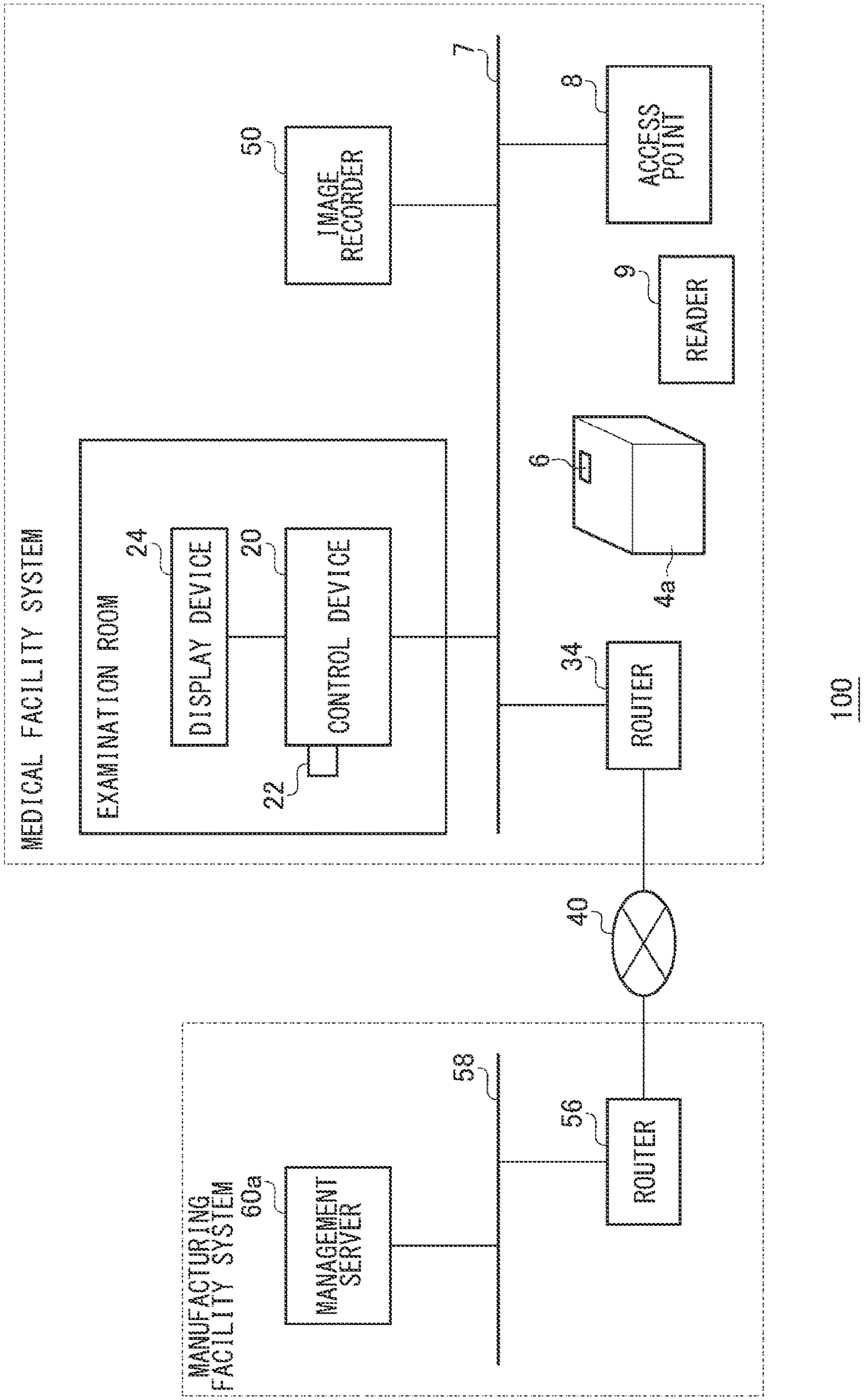
FIG. 17 is a diagram showing another example of the configuration of a medical instrument control system 100.

In the embodiments, the management server 60 may be provided in the medical facility 2 and may be communicatively connected to the control device 20 by the network 7. Alternatively, the management server 60 may be configured as a cloud server, for example. FIG. 17 shows another example of the configuration of a medical instrument control system 100. In this configuration example, the medical instrument control system 100 includes a manufacturing facility system managed by the manufacturing facility 1 and a medical facility system managed by the medical facility 2, and the manufacturing facility system and the medical facility system are communicably connected by the Internet 40.

The medical facility system is provided in the medical facility 2 and includes a control device 20, an image recorder 50, and an access point 8. The control device 20, the image recorder 50, and the access point 8 are communicatively connected by a network 7 such as a local area network (LAN). The network 7 is connected to the Internet 40 via a router 34.

The control device 20 is provided in an examination room. An endoscope, which is a medical instrument, is connected to a connection 22, and the control device 20 controls the functions of the endoscope. The control device 20 captures the image at the time when the release switch is operated and transmits the captured image to the image recorder 50. The image recorder 50 is an image server that records images captured during an endoscopic examination and stores images transmitted from the control device 20 in association with an examination order.

In the configuration example shown in FIG. 17, a manufacturing facility system includes a management server 60*a*. The management server 60*a* has the configuration of the management server 60 shown in FIG. 5. The management server 60*a* becomes connected to a network 58 such as a local area network (LAN) and becomes connected to the Internet 40 via a router 56. The management server 60*a* may receive environmental information and the like from a sensor unit 6 via a medical facility system.

In the embodiments, the authorization information generation unit 66 compares environmental information obtained at the time of transportation with environmental conditions suitable for transportation and generates authorization information indicating whether the use of an endoscope is permitted or prohibited based on the comparison results. In the exemplary variations, the authorization information generation unit 66 may compare environmental information obtained at the time of transportation with environmental conditions suitable for storage of medical instruments and generate authorization information. In other words, in the exemplary variations, the authorization information generation unit 66 may compare the threshold values of environmental elements set to guarantee the quality of medical instruments during storage with environmental information at the time of transportation so as to generate authorization information.

Environmental conditions suitable for use in medical operations such as examinations are set for medical instruments in order to guarantee their quality. The environmental conditions suitable for use are defined by the threshold values of environmental elements, and the quality of the medical instruments is guaranteed when the medical instruments are used in an environment where the threshold values are not exceeded. Usually, the environmental conditions suitable for use are set more strictly than those suitable for transportation, and the proper range of environmental conditions is narrower. In the exemplary variations, the authorization information generation unit 66 may compare environmental information obtained at the time of transportation with a value set based on the threshold value of an environmental element set at the time of use so as to generate authorization information. The value set based on the threshold value of the environmental element set at the time of use may be set to a value exceeding the threshold value of the environmental element set at the time of use, i.e., a value exceeding the proper range of environmental conditions suitable for use.

The authorization information generation unit 66 generates non-permission information indicating that the use of endoscopes is prohibited when the environmental information at the time of transportation exceeds predetermined threshold values defined by the set environmental conditions in the embodiments. When the authorization information generation unit 66 generates the non-permission information, the management server 60 may implement a process to arrange for a substitute for the endoscope. More specifically, the management server 60 may perform a process of ordering the manufacturing facility 1 or the like an endoscope of the same or similar type as the endoscope that has been prohibited from use.

In the embodiments, it is explained that the sensor 12 of a sensor unit 6 may detect temperature, acceleration, deceleration, humidity, illumination, and atmospheric pressure as environmental elements at the time of transportation. The sensor 12 may further detect the amount of change in temperature and humidity, the actual route (position) of transportation, radiation levels, etc. The sensor unit 6 may also detect the number of individual packaging boxes 5 contained in an accommodating container 4*a*. Furthermore, the control unit 10 may be able to acquire detected values from a gas sensor that detects the type and concentration of gas in a sterilization pack.

What is claimed is:

1. A medical instrument control system comprising:
a first accommodating container configured to accommodate a first medical instrument;
a first sensor configured to detect a value of an environmental element at a time of transportation of the first accommodating container;
a memory configured to record the value of the environmental element detected by the first sensor; and
one or more processors comprising hardware, wherein the one or more processors are configured to:
identify a transportation route used when the value of the environmental element detected by the first sensor provided to the first accommodating container exceeds a predetermined threshold value and identify a second accommodating container transported on the transportation route identified;
generate first authorization information indicating that use of a second medical instrument accommodated in the second accommodating container is not permitted, even if a value of the environmental element detected by a second sensor provided to the second accommodating container does not exceed the predetermined threshold value; and
restrict one or more functions of the second medical instrument based on the first authorization information.

2. The medical instrument control system according to claim 1,
wherein the one or more processors are configured to:
perform a comparison between the value of the environmental element detected by the first sensor associated with identification information of the first medical instrument and the predetermined threshold value; and
generate the first authorization information based on a result of the comparison.

3. The medical instrument control system according to claim 2,
wherein the predetermined threshold value is a value of the environmental element set to guarantee a quality of the first medical instrument at the time of transportation or at a time of storage.

4. The medical instrument control system according to claim 2,
wherein the predetermined threshold value is a value set based on a threshold value of the environmental element set at a time of use of the first medical instrument.

5. The medical instrument control system according to claim 2,
wherein the one or more processors are configured to:
in response to the result of the comparison being the value of the environmental element detected by the first sensor at the time of transportation exceeds the predetermined threshold value, generate the first authorization information, the first authorization information also indicating that use of the first medical instrument is not permitted; and
in response to the result of the comparison being the value of the environmental element detected by the first sensor at the time of transportation does not exceed the predetermined threshold value, generate a second authorization information indicating that the use of the first medical instrument is permitted.

6. The medical instrument control system according to claim 1,
wherein the one or more processors are configured to:
receive the value of the environmental element detected by the first sensor;
record the value of the environmental element detected by the first sensor in the memory in association with identification information of the first medical instrument;
acquire the identification information of the first medical instrument scheduled to be used for a medical operation; and
restrict one or more functions of the first medical instrument based on the value of the environmental element detected by the first sensor recorded in association with the acquired identification information.

7. The medical instrument control system according to claim 6, further comprising:
a reader configured to:
read the value of the environmental element detected by the first sensor; and
transmit the read value of the environmental element detected by the first sensor to the one or more processors.

8. The medical instrument control system according to claim 6,
wherein the first sensor is configured to transmit the value of the environmental element to the one or more processors.

9. The medical instrument control system according to claim 6,
wherein the first sensor is provided in the first accommodating container and is configured to hold an identification information of the first medical instrument accommodated in the first accommodating container, and
wherein the one or more processors are configured to receive the value of the environmental element detected by the first sensor and the identification information of the first medical instrument held by the first sensor.

10. The medical instrument control system according to claim 9,
wherein the first accommodating container is configured to accommodate a plurality of medical instruments including the first medical instruments, and
wherein the first sensor is configured to hold identification information of the plurality of medical instruments accommodated in the first accommodating container.

11. The medical instrument control system according to claim 6,
wherein the first sensor is configured to hold identification information of the first sensor, and
wherein the one or more processors are configured to:
receive the value of the environmental element detected by the first sensor and the identification information of the first sensor held by the first sensor; and
record the identification information of the first medical instrument and the value of the environmental element detected by the first sensor in with the identification information of the first sensor.

12. The medical instrument control system according to claim 1,
wherein the memory is provided in the first medical instrument and is configured to record an identification information of the first medical instrument and the value of the environmental element detected by the first sensor, and wherein the one or more processors are configured to:

acquire the identification information of the first medical instrument and the value of the environmental element recorded in the memory; and determine whether or not to generate the first authorization information based on the identification information of the first medical instrument and the value of the environmental element.

13. The medical instrument control system according to claim 1, wherein the first sensor is provided in for each first medical instrument.

14. The medical instrument control system according to claim 1, further comprising: a server that wherein the one or more processors are configured to:

determine to prohibit use of one or more of the first medical instrument and the second medical instrument based on a result of comparison between the value of the environmental element detected by the first sensor associated with identification information of the one or more of the first medical instrument and the second medical instrument and the predetermined threshold value; and arrange for a substitute for the one or more of the first medical instrument and the second medical instrument determined to be prohibited from use.

15. The medical instrument control system according to claim 1, wherein the first medical instrument includes a single-use endoscope.

16. A management server comprising:

one or more processors comprising hardware, the one or more processors being configured to:

identify a transportation route used when a value of an environmental element detected, by a first sensor, at a time of transportation of a first accommodating container that accommodates a first medical instrument exceeds a predetermined threshold value and identify a second accommodating container transported on the transportation route;

generate first authorization information indicating that use of a second medical instrument accommodated in the second accommodating container is not permitted, even if a value of the environmental element detected by a second sensor provided to the second accommodating container does not exceed the predetermined threshold value; and restrict one or more functions of the second medical instrument based on the first authorization information.

17. The management server according to claim 16, wherein the one or more processors are configured to receive the value of the environmental element from a reader that has read the value of the environmental element detected by the first sensor.

18. The management server according to claim 16, wherein the one or more processors are configured to receive the value of the environmental element from the first sensor.

19. A medical instrument control system comprising:

an accommodating container configured to accommodate a medical instrument;

a sensor configured to detect a value of an environmental element obtained at a time of transportation of the accommodating container;

a memory configured to record the value of the environmental element detected by the sensor associated with identification information of the medical instrument; and one or more processors comprising hardware, wherein the one or more processors are configured to:

determine to prohibit use of the medical instrument based on a result of comparison between the value of the environmental element associated with the identification information of the medical instrument and a predetermined threshold value; and in response to determining to prohibiting the use of the medical instrument based on the result of the comparison:

restrict one or more functions of the medical instrument; and implement a process to arrange for a substitute for the medical instrument.

* * * * *